United States Patent [19]
Linn et al.

[11] Patent Number: 5,169,839
[45] Date of Patent: Dec. 8, 1992

[54] DERIVATIVES OF 3'- AND 3"-O-DESMETHYL AVERMECTIN COMPOUNDS, COMPOSITIONS AND METHODS OF TREATING MELMINTIC AND PARASITIC INFECTIONS

[75] Inventors: Bruce O. Linn, Bridgewater; Helmut Mrozik, Matawan, both of N.J.

[73] Assignee: Merck & Co., Inc., Rahway, N.J.

[21] Appl. No.: 521,961

[22] Filed: May 11, 1990

[51] Int. Cl.$^5$ ............ A61K 31/70; C07H 17/04
[52] U.S. Cl. ........................ 514/30; 536/7.1
[58] Field of Search ................ 536/7.1; 574/30

[56] References Cited

U.S. PATENT DOCUMENTS

| | | | |
|---|---|---|---|
| 4,199,569 | 4/1980 | Chabala et al. | 514/30 |
| 4,201,861 | 5/1980 | Mrozik et al. | 536/7.1 |
| 4,289,760 | 9/1981 | Mrozik et al. | 514/30 |
| 4,427,663 | 1/1984 | Mrozik | 514/30 |
| 4,997,383 | 1/1990 | Sinclair | 514/30 |

FOREIGN PATENT DOCUMENTS 375395 6/1990 European Pat. Off. .

OTHER PUBLICATIONS

Schulman et al (I), The Journal of Antibiotics 38, pp. 1494–1498 (1988).
Schulman et al (II), Antimicrobial Agents and Chemotherapy, pp. 744–747 (1987).

*Primary Examiner*—Johnnie R. Brown
*Assistant Examiner*—Elli Peselev
*Attorney, Agent, or Firm*—David L. Rose; Joseph F. DiPrima

[57] ABSTRACT

There are disclosed derivatives of avermectin compounds wherein one or both of the 13-oleandrose saccharide groups lack the methyl group of the 3'- or 3"-methoxy. Such compounds are potent anthelmintic and antiparasitic agents.

10 Claims, No Drawings

DERIVATIVES OF 3'- AND 3"-O-DESMETHYL AVERMECTIN COMPOUNDS, COMPOSITIONS AND METHODS OF TREATING MELMINTIC AND PARASITIC INFECTIONS

BACKGROUND OF THE INVENTION

Desmethyl avermectin compounds wherein one or both of the oleandrose saccharide groups are demethylated are disclosed in Schulman et. al. in *The Journal of Antibiotics*, 38, 1494–1498 (1985). Such compounds are natural products produced by the fermentation of a strain of *Streptomyces avermitilis* in the presence of sinefungin. The instant compounds are derivatives of the compounds disclosed in Schulman et. al. Other avermectins missing one or both of the 3'-O- and 3"-O-methyl groups are disclosed in EPO published application 276131, and derivatives of these compounds are also used as starting materials for the compounds of this invention. It is known from Schulman et. al. that such avermectin derivatives missing one or both of the 3'-O- and 3"-O-methyl groups have reduced potency as anthelmintic agents. However certain derivatives obtained through chemical modification of these compounds have highly potent antiparasitic and insecticidal activity.

SUMMARY OF THE INVENTION

This invention is concerned with novel avermectin compounds derived from 3'- and 3"-O-desmethyl starting materials. Thus, it is an object of this invention to describe such compounds and processes for their preparation. A further object of this invention is to describe the use of such compounds in the treatment of parasitic infections. A still further object of this invention is to describe compositions for such use using the described compounds as the active agent thereof. Further objects will become apparent from a reading of the following description.

DESCRIPTION OF THE INVENTION

The novel compounds of the instant invention are best realized in the following structural formula.

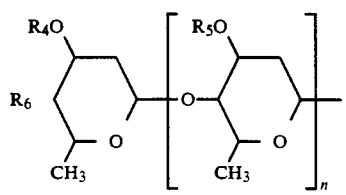

-continued

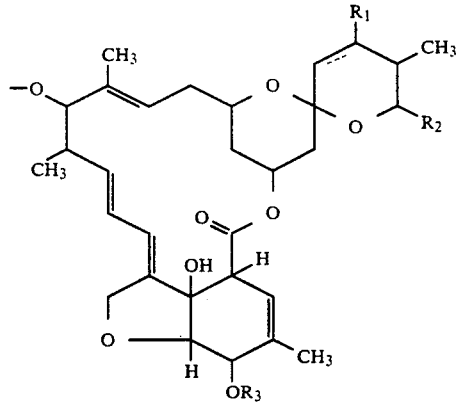

wherein the broken line at the 22,23 positions indicates that either a single or a double bond is present at the 22,23 position and that $R_1$ is present only when the broken line indicates a 22,23-single bond;

n is 0 or 1;

$R_1$ is hydrogen, hydroxy or a 23-oxo group;

$R_2$ is an α-branched $C_3$–$C_8$ alkyl, alkenyl, alkoxyalkyl or alkylthioalkyl; a $C_5$–$C_8$ cycloalkyl $C_1$–$C_4$ alkyl group, a $C_3$–$C_8$ cycloalkyl or a $C_5$–$C_8$ cycloalkenyl, each of which may be optionally substituted by methylene, or one or more $C_1$–$C_4$ alkyl groups or halogen; or a 3 to 6 membered oxygen or sulfur containing heterocycle which may be saturated or fully or partly unsaturated and which may be substituted by one or more $C_1$–$C_4$ alkyl groups or halogen atoms;

$R_3$ is hydrogen, methyl, loweralkanoyl, loweralkylcarbonyl, or triloweralkylsilyl;

$R_4$ and $R_5$ are independently hydrogen, methyl, loweralkanoyl, benzoyl, loweralkoxy carbonyl, phenoxycarbonyl, carbamoyl, N-loweralkyl carbamoyl, or N,N-diloweralkylcarbamoyl or loweralkoxyloweralkyl, provided that both $R_4$ and $R_5$ are hydrogen only when $R_6$ is other than hydroxy and provided that both $R_4$ and $R_5$ are not simultaneously methyl; and $R_6$, with the broken line indicating a single bond to $R_6$ is hydroxy, amino, N-loweralkylamino, N,N-diloweralkylamino, loweralkanoylamino, N-loweralkanoyl-N-loweralkylamino, loweralkoxycarbonylamino, triloweralkylsilyloxy, carbamoyloxy, N-lower-alkylcarbamoyloxy, N,N-diloweralkyl carbamoyloxy, loweralkoxymethoxy, loweralkanoyloxy, substituted loweralkanoyloxy such as succinoyloxy or acetylglycyloxy; or when the broken line indicates a double bond to $R_6$, $R_6$ is oxo, semicarbazono, loweralkanoyl hydrazono, benzoyl hydrazono, loweralkyl substituted benzoyl hydrazono or p-toluene sulfonylhydrazono;

Preferred compounds of this invention are realized in the foregoing structural formula when:

$R_1$ is hydrogen or hydroxy;

$R_2$ is an alpha-branched $C_3$–$C_8$ alkyl or alkenyl group;

$R_3$ is hydrogen or methyl.

$R_4$ and $R_5$ are independently hydrogen, methyl, loweralkanoyl, benzoyl, loweralkoxycarbonyl, loweralkoxyloweralkyl provided that both $R_4$ and $R_5$ are hydrogen only when $R_6$ is other than hydroxy and provided that both $R_4$ and $R_5$ are not simultaneously methyl; and R$_6$, with the broken line indicating a single bond, is hydroxy, amino, N-loweralkylamino, N,N-diloweralkylamino, loweralkanoylamino, N-loweralkanoyl-N-loweralkylamino, loweralkoxymethoxy or loweralkanoyloxy.

Additional preferred compounds of this invention are realized in the foregoing structural formula when:

R$_1$ is hydrogen or hydroxy;

R$_2$ is 2-propyl, 2-butyl, 2-pentyl, 2-hexyl, 2-buten-2-yl, 2-penten-2-yl, 4-methyl-2-penten-2-yl, cyclohexyl, cyclopentyl, 3-thienyl, 3-furyl, 1-methylthioethyl;

R$_3$ is hydrogen,

R$_4$ and R$_5$ are independently hydrogen, methylloweralkanoyl, loweralkoxyloweralkyl, loweralkoxycarbonyl, carbamoyl, N-loweralkylcarbamoyl, N,N-diloweralkylcarbamoyl, provided that both R$_4$ and R$_5$ are hydrogen only when R$_6$ is other than hydroxy provided that both R$_4$ and R$_5$ are not simultaneously methyl; and;

R$_6$, with the broken line indicating a single bond, is hydroxy, amino, N-methylamino, N,N-dimethylamino, acetylamino, ethoxymethoxy; acetoxy, succinoyloxy or acetylglycyloxy.

Additional preferred compounds, are realized when both R$_4$ and R$_5$ are other than hydrogen or methyl.

Preferred compounds of the instant invention are further realized in the following compounds:

3″-O-desmethyl-3″,4″-di-O-acetyl avermectin B1a/B1b;

3″-O-desmethyl avermectin B1a/B1b 3″,4″-O-carbonate ester;

3″-O-desmethyl-4″-O-succinoyl avermectin B1a/B1b;

4″-O-(acetylglycyl)-3″-O-desmethyl avermectin B1a/B1b;

3″-O-desmethyl-4″-O-[(dimethylamino)carbonyl]avermectin B1a/B1b;

3″-O-desmethyl-4″-deoxy-4″-(methylamino) avermectin B1a/B1b;

3″-O-desmethyl-4″-deoxy-4″-epi(methylamino) avermectin B1a/B1b;

3′,3″-O-bis-desmethyl-3′,4″-di-O-methoxymethyl avermectin B1a/B1b;

3′,3″-bis-o-desmethyl-25-cyclohexyl-25-de-(2-butyl)-3′,4″-di-O-methoxymethylavermectin B2a;

3′,3″-bis-O-desmethyl-25-cyclopentyl-25-de-(2-butyl)-3′,4″-di-O-methoxymethylavermectin B2a;

3′,3″-bis-O-desmethyl-25-(3-thienyl)-25-de-(2-butyl)-3′,4″-di-O-methoxymethylavermectin B2a;

3′,3″-bis-O-desmethyl-25-(3-furyl)-25-de-(2-butyl)-3′,4″-di-O-methoxymethylavermectin B2a;

3′,3″-bis-O-desmethyl-25-(1-methylthioethyl)-25-de-(2-butyl)-3′,4″-di-O-methoxymethylavermectin B1a;

3″-acetylamino-3″-deoxy-3′,3″-bis-O-desmethyl-3′,4″-di-O-methoxymethylavermectin B1a/B1b;

4″-O-acetyl-3′,3″-bis-O-desmethylavermectin B1a/B1b;

3′-O-desmethylavermectin B1a/B1b monosaccharide;

3′-O-desmethyl-4′-O-methoxymethylavermectin B1a/B1b monosaccharide.

In the instant description of the invention, the term "loweralkyl" is intended to include those alkyl groups of from 1 to 6 carbon atoms in either a straight or branched configuration. Examples of such alkyl groups are methyl, ethyl, propyl, isopropyl, butyl, sec-butyl, pentyl, hexyl and the like.

The term loweralkoxy is intended to include those alkoxy groups of from 1 to 6 carbon atoms in either a straight or branched configuration. Examples of such alkoxy groups are methoxy, ethoxy, propoxy, butoxy, tertbutoxy, pentoxy, hexoxy and the like.

The term "loweralkanoyl" is intended to include those alkanoyl groups containing from 1 to 6 carbon atoms in either a straight or branched configuration. Examples of such alkanoyl groups are formyl, acetyl, propoyl, butyryl, isobutyryl, pentanoyl, hexanoyl and the like. Preparation of starting materials.

The compounds used as starting materials for the instant invention are produced through artificial modification of the fermentation of *Streptomyces avermitilis* either by addition of metabolic inhibitors such as cinefungin (as described by Schulman et al., *J. Antibiot.* 1985, 38, 1494–1498) or by mutation of the parent strain (as described by Schulman et al., *Antimicrobial Agents and Chemotherapy*, 1987, 31, 744–747, and by EP-276-131-A to Pfizer Inc.). Avermectin derivatives missing one or two of the 3′- and 3″-O-methyl groups have reduced anthelmintic potencies (Schulman et al., *J. Antibiot.* 1985, 38, 1494–1498). It was now found that derivatives of such 3′- or 3″-O-desmethylavermectin, derivatives, however, are very potent anthelmintic agents.

The instant compounds with an acyl function at the 5, 4′, 4″, 3′, 3″, or 23 positions are prepared by acylating the various hydroxy groups at such positions of the 3′- or 3″-O-desmethyl avermectin compounds. In particular the 5-hydroxy, 4′-hydroxy, 4″-hydroxy, 3′-hydroxy, 3″-hydroxy or the 23-hydroxy groups can be reacted with acylating agents to prepare the appropriate acylated derivative, such as the loweralkanoyl, benzoyl, loweralkoxycarbonyl, phenoxycarbonyl, carbamoyl, N-loweralkylcarbamoyl, and N-diloweralkylcarbamoyl substituents. Such compounds are prepared using the appropriate reactive intermediates such as the acid chloride, anhydride, carbamoylchloride and the like. The reaction conditions for such reactions are generally well known to those skilled in the art and are further disclosed in U.S. Pat. No. 4,201,861 to Mrozik et. al. The 23-hydroxy group is more difficult to acylate and usually needs forcing conditions for its acylation. Thus it does not usually need to be protected when reacting other hydroxy groups on the molecule.

In addition, those compounds with a 23-keto function are prepared by the selective oxidation of the 23-hydroxy group with pyridinium dichromate, chromic acid-dimethyl pyrazole, and the like as disclosed in U.S. Pat. No. 4,289,760 to Mrozik et al.

The conversion of the 22,23-double bond into the reduced 22,23-single bond compound by the selective oxidation with Wilkinsons homogeneous catalyst, triphenylphosphine rhodium chloride is described in U.S. Pat. No. 4,199,569 to Chabala et. al.

The reactions which produce the various 4″ or 4′ derivatives such as the keto, amino and substituted amino involve the selective oxidation of the 4″ or 4′ hydroxy to 4″ or 4′ keto which is then reacted with an amino to prepare the amino compounds. These processes are detailed in U.S. Pat. No. 4,427,663 to Mrozik.

The 4″ or 4′ imino compounds are also prepared from the 4″ or 4′ keto compounds by reaction with the appropriately substituted semicarbazide, sulfonyl hydrazine and the like. The reaction is carried out in a non-reactive solvent at from 20° to 80° C. in from 30 minutes to 48 hours. The products are isolated using techniques known to those skilled in the art.

It is very often desirable to protect those reactive groups which are not intended to be reacted and it has been found that the trisubstituted silyl group is preferred, in particular tri-butyldimethylsilyl. The protected compounds are, however, significantly active anthelmintic agents and such silyl derivatives are intended to be within the ambit of this invention. The procedures for the preparation of such compounds is described in the foregoing cited patents.

The "b" compounds, those with a 25-iso-propyl group, may be somewhat difficult to separate from the corresponding "a" compound with a 25-sec-butyl group and as such the compounds are generally isolated as mixtures of the two compounds. Thus references in the instant application to "a" compounds such as B1a, A1a, and the like, are construed to actually contain a certain proportion of the corresponding "b" compound. Alternatively, this representation of a mixture is sometimes done by referring to the B1 or B2 compounds without specifically designating "a" or "b" compounds, or by separating the "a" compound from the "b" compound by a slash (/) such as B1a/B1b, B2a/B2b and the like.

The novel compounds of this invention have significant parasiticidal activity as anthelmintics, ectoparasiticides, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia and Oesphagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The substituted avermectin compounds of this invention have unexpectedly high activity against these parasites, and in addition are also active against Dirofilaria in dogs, Namatospiroides, Syphacia, Aspiculuris in rodents, arthropod ectoparasites of animals and birds such as ticks, mites, lice, fleas, blowfly, in sheep Lucilia sp., biting insects and such migrating diperous larvae as Hypoderma sp. cattle, Gastrophilus in horses, and Cuterebra sp. in rodents.

The instant compounds are also useful against parasites which infect humans. The most common genera of parasities of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., and the housefly *Musca domestica.*

The compounds are also useful against insect pests of stored grains such as Tribolium sp., Tenebrio sp. and of agricultural plants such as spider mites, (Tetranychus sp.), aphids, (Acyrthiosiphon sp.); against migratory orthopterans such as locusts and immature stages of insects living on plant tissue. The compounds are useful as a nematocide for the control of soil nematodes and plant parasites such as Meloidogyne spp. which may be of importance in agriculture. The compounds are active against other plant pests such as the southern army worm and Mexican bean beetle larvae.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the avermectin derivatives in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, and aqueous parenteral formulations are also used. The active avermectin compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1–5 days. With the preferred compounds of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active hydrogenated avermectin compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular avermectin derivative employed, the compounds of this invention are usually fed at concentrations of between 0.00001 to 0.002% in the feed in order to achieve the desired antiparasitic result.

The avermectin compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

In using the compounds of this invention, the individual substituted avermectin components may be prepared and used in that form. Alternatively, mixtures of two or more of the individual avermectin components may be used, as well as mixtures of the parent avermectin compounds, other avermectin compounds or other active compounds not related to avermectin, with the compounds of this invention.

The products of this invention may be used in any of a variety of pharmaceutical preparations. They may be employed in capsule, powder form, in liquid solution, or in suspension. They may be administered by a variety of means; those of principal interest include: orally, topically or parenterally by injection (intravenously, subcutaneously or intramuscularly).

Such tablets and capsules, designed for oral administration, may be in unit dosage form, and may contain conventional excipients, such as binding agents, for example, syrup, acacia, gelatin, sorbitol, tragacanth, or polyvinylpyrrolidone; fillers, for example, lactose, sugar, cornstarch, calcium phosphate, sorbitol, or glycerine; lubricants, for example, magnesium stearate, talc, polyethylene glycol, silica; disintegrants, for example, potato starch, acceptable wetting agents such as sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose. Suppositories will contain conventional suppository bases, such as cocoa butter or other glycerides.

Compositions for injection, the preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstiution, at the time of delivery, with a suitable vehicle, such as sterile water.

The compositions may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semi-solid form. Topical applications may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibiotic art. In general, a daily dosage consists of from about 0.1 to about 5 mg of active ingredient per kg. ob body weight of the subject in one or more treatments per day. A preferred daily dosage for mature animals lies in the range of from about 0.1 to 20 mg. of active ingredient per kg. of body weight. Another factor influencing the precise dosage regimen, apart from the nature of the infection and peculiar identity of the individual being treated, is the molecular weight of the chosen species of this invention.

The compositions for delivery per unit dosage, whether liquid or solid, may contain from 0.1% to 99% of active material, the preferred range being from about 10-60%. The composition will generally contain from about 5 mg. to about 50 mg. of the active ingredient; however, in general, it is preferable to employ a dosage amount in the range of from about 5 mg to 100 mg. In parenteral administration, the unit dosage is usually the pure compound I in sterile solution or in the form of a soluble powder intended for solution.

In the isolation of the avermectin compounds, which serve as starting materials for the instant process, from the fermentation broth, the various avermectin compounds will be found to have been prepared in unequal amounts. In particular an "a" series compound will be prepared in a higher proportion than the corresponding "b" series compound. The difference between the "a" series and "b" series is constant throughout the avermectin compounds and consists of a sec-butyl group and an iso-propyl group respectively at the 25 position. This difference, of course, does not interfere with any of the instant reactions. In particular it may not be necessary to separate the "b" components from the related "a" component. Separation of these closely related compounds is generally not practiced since the "b" compound is present only in a very small percent by weight, and the structural difference has negligible effect on the reaction processes and biological activities.

In particular it has been found that the starting materials for the compounds of this invention are very often prepared in a ration of about 80% avermectin B1a or A1a and 20% avermectin B1b or A1b. Thus the preferred composition of this invention is one which contains more than about 80% of the "a" component and less than about 20% of the "b" component.

The following examples are provided in order that this invention might be more fully understood; they are not to be construed as limitative of the invention.

The substituted avermectin derivatives prepared in the following examples are generally isolated as amorphous solids and not as crystalline solids. They are thus characterized analytically using techniques such as mass spectrometry, nuclear magnetic resonance, and the like. Being amorphous, the compounds are not characterized by sharp melting points, however, the chromatographic and analytical methods employed indicate that the compounds are pure.

EXAMPLE 1

5-O-t-Butyldimethylsilyl-3''-O-desmethyl avermectin B1a/B1b

To a solution of 3''-O-desmethyl avermectin B1a/B1b (1.0 g, 1.15 mmole) in 10 mL of dimethylformamide is added imidazole (235 mg, 3.45 mmole) followed by t-butyldimethylsilylchloride, (260 mg, 1.725 mmole). The reaction mixture is stirred at room temperature for ½ to 1 hour until silica gel thin layer chromatography (methylene chloride-ethyl acetate solvents) shows the reaction as completed. Water (50 mL) and ether (120 mL) is added to the reaction mixture, the layers are separated, the ether layer is washed twice with water, dried and concentrated in vacuo. Further purification by column chromatography (silica gel, methylene chloride-ethyl acetate solvents) affords the pure title compound which is characterized by $^1$H NMR and mass spectrometry.

EXAMPLE 2

5-O-t-Butyldimethylsilyl-3''-O-desmethyl-3'',4''-di-O-acetyl avermectin B1a/B1b

A solution of 5-O-t-butyldimethylsilyl-3''-desmethyl avermectin B1a/B1b (100 mg, 0.1 mmole) in puridine (1.8 mL) and acetic anhydride (0.2 mL, 2 mmole) is held at room temperature for 4 hours while the progress of the reaction is observed by thin layer chromatography. Then 10 mL of ice water is added and the solid residue is collected by filteration. The solid product is dissolved in ether and washed with water and diluted aqueous sodium bicarbonate solution. The ether extract is dried and concentrated to a white foam. The foam is purified by preparative thick (1 mm) layer silica gel chromatography (methylene chloride, ethyl acetate solvents) to give pure 5-O-t-butyldimethylsilyl-3''-desmethyl-3'',4''-di-O-acetyl avermectin B1a/B1b which is characterized by $^1$H NMR and mass spectrometry.

EXAMPLE 3

3''-O-Desmethyl-3'',4''-di-O-acetyl avermectin B1a/B1b

A solution of 5-O-t-butyldimethylsilyl-3''-O-desmethyl-3'',4''-O-di-acetyl avermectin B1a/B1b (50 mg, 0.05 mmole) in methanol (5.0 mL) containing p-toluence sulfonic acid monohydrate (50 mg, 1% solution) is kept at room temperature for 20 to 30 minutes. Then ethyl acetate (95 mL) is added and the solution is washed immediately with dilute aqueous sodium bicarbonate solution (3 times) in water. The organic extract is dried and concentrated in vacuo to a light foam. The residue is purified by preparative layer chromatography on silica gel (methylene chloride, tetrahydrofuran, ethanol solvents) to give pure 3''-desmethyl-3'',4''-di-O-acetyl avermectin B1a/B1b identified by $^1$H NMR and mass spectrometry.

EXAMPLE 4

5-O-t-Butyldimethylsilyl-3''-O-desmethyl avermectin B1a/B1b-3'',4''-O-carbonate ester A solution containing 5-O-t-butyldimethylsilyl-3''-O-desmethyl avermectin B1a/B1b (100 mg, 0.1 mmole), triethylamine (0.03 mL, 22 mg, 0.27 mmole) and 1,1' carbonyl diimidazole (25 mg, 1.5 mmole) in 10 mL of acetonitrile is stirred at room temperature for 18 hours. The reaction mixture is diluted with water (50 mL) and extracted with methylene chloride (150 mL). The organic extract is washed with water 3 times, dried and concentrated in vacuo. The residue is purified by preparative layer chromatography on silica gel (methylene chloride, ethyl acetate solvents) to give 5-O-t-butyldimethylsilyl-3''-O-desmethyl avermectin B1a/B1b-3'',4''-O-carbonate ester which is identified through its $^1$H NMR and mass spectra.

EXAMPLE 5

3''-O-Desmethyl avermectin B1a/B1b 3'',4''-O-carbonate ester

A solution is prepared containing 14 mL of tetrahydrofuran, 4 mL of pyridine and 2 mL of hydrogen fluoride-pyridine solution (available from Aldrich Chemical Company). 5-O-t-Butyldimethylsilyl-3''-O-desmethyl avermectin B1a/B1b (50 mg) dissolved in 0.6 mL of the tetrahydrofuran-pyridine-hydrogen fluoride solution is kept for 18 hours under nitrogen at room temperature. The reaction mixture is then poured on to 15 mL of diluted aqueous sodium carbonate solution, which is then extracted with ether. The ether extract is washed 3 times with water, dried and concentrated in vacuo. The residue is then further purified on 1 mm thick silica gel preparative layer chromatography plates to give 3''-O-desmethyl avermectin B1a/B1b 3'',4''-O-carbonate ester identified by $^1$H NMR and mass spectra.

EXAMPLE 6

3''-O-Desmethyl-3'',5-di-O-t-butyldimethylsilyl avermectin B1a/B1b

In a modification of the procedure of Example 1, 3''-O-desmethyl avermectin B1a/B1b (1.0 g, 1.15 mmole), dimethylforamide, (10 mL) imdidazole (340 mg, 5.0 mmole) and t-butyldimethylsilyl chloride (375 mg, 2.5 mmole) is reacted at room temperature for 1½ to 3 hours. Work up by silica gel column chromatography and separation of the reaction mixture gives 3''-O-desmethyl-3'',5-di-O-butyldimethylsilyl avermectin B1a/B1b which is identified by $^1$H NMR and mass spectrometry.

EXAMPLE 7

3''-O-Desmethyl-3'',5-di-O-t-butyldimethylsilyl-4''-O-succinoyl avermectin B1a/B1b A solution of 100 mg of 3''-O-desmethyl-3'',5-di-O-t-butyldimethylsilyl avermectin B1a/B1b, 0.14 mL of diisopropylethylamine, 50 mg of 4-dimethylaminopiperidine and 42 mg of succinic anhydride in 1.6 mL of anhydrous methylene chloride is kept at room temperature for 24 hours. The reaction mixture is poured onto ice cold dilute aqueous sodium dihydrogen phosphate solution, extracted twice with methylene chloride (50 mL), and the organic phase is washed with water, dried and concentrated to a solid residue in vacuo. Purification by preparative layer silica gel chromatography gives 3''-O-desmethyl-3'',5-di-O-t-butyldimethylsilyl-4''-O-succinoyl avermectin B1a/B1b which is identified by $^1$H NMR and mass spectrometry.

EXAMPLE 8

3''-O-Desmethyl-4''-O-succinoyl avermectin B1a/B1b 50 mg of 3''-O-desmethyl-3'',5-di-O-t-butyldimethylsilyl-4''-O-succinoyl avermectin B1a/B1b is reacted according to the procedure of Example 5 affording 3''-O-desmethyl-4''-O-succinoyl avermectin B1a/B1b.

EXAMPLE 9

4''-O-(Acetylglycyl)-3''-O-desmethyl-3'',5-di-O-t-butyl-dimethylsilyl avermectin B1a/B1b A solution of 3''-O-desmethyl-3'',5-di-O-t-butyldimethylsilyl avermectin B1a/B1b (100 mg, 0.09 mmole), 4-(dimethylamino)pyridine (25 mg, 0.2 mmole), N-acetylglycine (24 mg, 0.2 mmole) and dicyclohexylcarbodiimide (46 mg, 0.22 mmole) in 1.5 mL of methylene chloride is stirred at room temperature for 2 hours. The reaction mixture is then filtered, diluted with methylene chloride and washed with water. The organic phase is dried, concentrated and purified by preparative layer chromatography on silica gel plates to provide 4''-O-(acetylglycyl)-3''-O-desmethyl-3'',5-di-O-t-butyldimethylsilyl avermectin B1a/B1b which is identified by $^1$H NMR and mass spectrometry.

EXAMPLE 10

4''-O-(Acetylglycyl)-3''-O-desmethyl avermectin B1a/B1b

4''-O-(acetylglycyl)-3''-O-desmethyl-3'',5-di-O-t-butyldimethylsilyl avermectin B1a/B1b (50 mg) is treated with a solution of hydrogen fluoride in pyridine and tetrahydrofuran according the procedure of Example 5 to provide 4''-O-(acetylglycyl)-3''-O-desmethyl avermectin B1a/B1b which is identified by $^1$H NMR and mass spectrometry.

EXAMPLE 11

3''-O-Desmethyl-3'',5-di-O-t-butyldimethylsilyl-4''-O-[[(4-nitrophenyl)-oxy]carbonyl] avermectin B1a/B1b A solution of 3''-O-desmethyl-3'',5-di-O-t-butyldimethylsilyl avermectin B1a/B1b from Example 6 (110 mg, 0.1 mmole), 4-(dimethylamino)pyridine (50 mg, 0.4 mmole) and diisopropylethylamine (50 mg, 0.4 mmole) in 2.5 mL of methylene chloride is stirred in an ice bath. A solution of 4-nitrophenyl chloroformate (0.3 mmole, 60 mg) in 0.5 mL methylene chloride is added via a syringe through a rubber septum. After 1 hour at 0° C., ice is added, and the reaction is worked up by extraction with methylene chloride. The extract is washed with water, dried and concentrated in vacuo. The residue is purified by preparative layer chromatography on silica gel and 3''-O-desmethyl-3'',5-di-O-t-butyldimethylsilyl-4''-O-[[(4-nitrophenyl)-oxy]carbonyl] avermectin B1a/B1b is isolated and characterized by $^1$H NMR and mass spectrometry.

EXAMPLE 12

3''-O-Desmethyl-3'',5-di-O-t-butyldimethylsilyl-4''-O-[(dimethylamino)carbonyl] avermectin B1a/B1b A solution of 3''-O-desmethyl-3'',5-di-O-t-butyldimethylsilyl-4''-O-[[(4-nitrophenyl)oxy]carbonyl] avermectin B1a/B1b (55 mg) in 4.0 mL of ether is cooled in a ice bath while dimethylamine is bubbled into the solution in a rapid stream for about 1 minute. The reaction mixture is kept for 30 minute at 0° C. and is then evaporated under a stream of nitrogen. The residue is taken up in ether, washed with water and concentrated in vacuo. The crude product is purified by preparative layer chromatography on silica gel to give 3''-O-desmethyl-3'',5-di-O-t-butyldimethylsilyl-4''-O-[(dimethylamino)carbonyl] avermectin B1a/B1b which is identified by $^1$H NMR and mass spectrometry.

EXAMPLE 13

3''-O-Desmethyl-4''-O-[(dimethylamino)carbonyl] avermectin B1a/B1b

3''-O-Desmethyl-3'',5-di-O-t-butyldimethylsilyl-4''-O-[(dimethylamino)carbonyl] avermectin B1a/B1b is treated with a hydrogen fluoride-pyridine-tetrahydrofuran solution according to the procedure of Example 5 to give 3''-O-desmethyl-4''-O-[(dimethylamino)-carbonyl] avermectin B1a/B1b which is identified its $^1$H NMR and mass spectrometry.

EXAMPLE 14

3''-O-Desmethyl-3'',5-di-O-t-butyldimethylsilyl-4''-oxo-avermetcin B1a/B1b

A mixture of 0.3 mL of methylene chloride and 20 ml of oxalyl chloride is placed in a dry flask under nitrogen and cooled to −60° C. From a syringe through a rubber septum 0.2 mL of methylene chloride solution containing 32 mL of dimethylsulfoxide is added over 3 minutes while the reaction is stirred at −60° C. Then a solution of 100 mg of 3''-O-desmethyl-3'',5-di-O-t-butyldimethylsilyl avermectin B1a/B1b (as obtained from Example 6) in 0.6 mL of methylene chloride is added dropwise over 5 minutes and the resulting mixture is stirred at −60° C. for 30 minutes. Then 0.15 mL of triethylamine is added dropwise over 10 minutes at −60° C. Then the cooling bath is removed and the reaction mixture is allowed to come to room temperature over a period of approximately 1 hour. Then 10 mL, of water is added and the product is extracted with ether. The ether solution is washed with water, dried and concentrated under high vacuum. The solid residue is purified by preparative layer chromatography on silica gel (methylene chloride, ethyl acetate solvents) to give 3''-O-desmethyl-3'',5-di-O-t-butyldimethylsilyl-4''-oxo-avermectin B1a/B1b which is characterized by $^1$H NMR and mass spectrometry.

EXAMPLE 15

3''-O-desmethyl-3'',5-di-O-t-butyldimethylsilyl-4''-deoxy-4''-(methylamino)avermectin B1a/B1b A solution of 0.1 mL of acetic acid in 1.5 mL of methanol is stirred in an ice bath. Methylamine is bubbled into the solution until the pH is between 8 and 9. Then a solution of 200 mg of 3''-O-desmethyl-3'',5-di-t-butyldimethylsilyl-4''-oxo-avermectin B1a/B1b (from Example 14) in 1.0 mL of methanol is added and the ice bath is removed. The reaction mixture is stirred for 1 hour at room temperature. Then a solution of 16 mg of sodium cyanoborohydride in 0.33 mL of methanol is added and stirring continued for about 1 hour. The reaction mixture is poured onto 7 mL of cold aqueous sodium bicarbonate solution. The crude products are extracted twice with 50 mL of ether and the combined ether extracts washed twice with water (10 mL), dried and concentrated in high vacuum. The solid residue is then applied to four preparative layer chromatography plates (1 mm silica gel) and developed with ethyl acetate. The two slow moving bands are removed separately and extracted from the silica gel with a mixture of ethyl acetate and ethanol (2:1) to give pure 3''-O-desmethyl-3'',5-di-O-t-butyldimethylsilyl-4''-deoxy-4''-(methylamino)avermectin B1a/B1b as the minor product and its 4''-epi isomer as the major product. The two epimeric methylamine products are identified by $^1$H NMR and mass spectrometry. 3''-O-desmethyl-3'',5-di-O-t-butyldimethylsilyl-4''-deoxy-4''-(methylamino)avermectin B1a/B1b has a signal in the nuclear magnetic resonance spectrum at 2.68 ppm (narrow multiplet, less than 2 Hertz wide) and the 4''-epi-3''-O-desmethyl-3'',5-di-O-t-butyldimethylsilyl-4''-deoxy-4''-(methylamino)avermectin B1a/B1b is identified by a triplet centered at 2.15 ppm with a coupling constant of 9 Hertz.

EXAMPLE 16

3''-O-Desmethyl-4''-deoxy-4''-(methylamino)avermectin B1a/B1b

3''-O-Desmethyl-3'',5-di-O-t-butyldimethylsilyl-4''-deoxy-4''-(methylamino)avermectin B1a/B1b is deprotected with a hydrogen fluoride-pyridine-tetrahydrofuran solution according the procedure of Example 5 to give the title compound which is characterized by $^1$H NMR and mass spectrometry.

EXAMPLE 17

3''-O-Desmethyl-4''-deoxy-4''-epi(methylamino)avermectin B1a/B1b

3''-O-Desmethyl-3'',5-di-O-t-butyldimethylsilyl-4''-deoxy-4''-epi(methylamino) avermectin B1a/B1b from Example 15 is reacted according to the procedure of Example 5. The title compound is obtained and indentified by $^1$H NMR and mass spectrometry.

EXAMPLE 18

3''-O-tert-Butyldimethylsilyl-3',3''-bis-O-desmethylavermectin B1a/B1b;
5-O-tert-butyldimethylsilyl-3',3''-bis-O-desmethyl-avermectin B1a/B1b;
3'',5-di-O-tert-butyldimethylsilyl-3',3''-bis-O-desmethylavermectin B1a/B1b, and
3',3'',5-tri-O-tert-butyldimethylsilyl-3',3''-bis-O-desmethyl avermectin B1a/B1b Tert.-butyldimethylsilyl chloride, 338 mg, was added to 1.00 g of 3',3''-bis-O-desmethylavermectin B1a/B1b and 434 mg of imidazole in 30 ml of dry dimethylformamide and the solution was stirred at room temperature, 23° C., for 28 hours. The reaction mixture was diluted with methylene chloride and extracted with water. The methylene chloride solution was dried over sodium sulfate and evaporated under reduced pressure. The residue was chromatographed on a column of silica gel using 1 to 3% methanol in methylene chloride furnishing 400 mg of 3''-O-tert.-butyldimethylsilyl-3',3''-bis-O-desmethylavermectin B1a/B1b (molecular ion plus lithium peak identified by fast atom bombardment (FAB) mass spectrometry [(M+Li)+ =965] 241 mg of 5-O-tert.-butyldimethylsilyl-3',3''-bis-O-desmethylavermectin B1a/B1b, [(M+Li)+ =965], 370 mg of 3'',5-di-O-tert.-butyldimethylsilyl-3',3''-bis-O-desmethylavermectin B1a/B1b [(M+Li)+ =1079], and 55 mg of 3',3'',5-tri-O-tert.-butyldimethylsilyl-3',3''-bis-O-desmethylavermectin B1a/B1b [(M+Li)+ =1193]. These products were fully characterized by nuclear magnetic resonance, mass spectra and high pressure liquid chromatographic analyses.

EXAMPLE 19

3'',5-di-O-tert-butyldimethylsilyl-3',3''-bis-O-desmethyl-3',4''-di-O-methoxymethylavermectin B1a/B1b Chloromethyl methyl ether, 25 microliters, was added to 36 mg of 3'',5-di-O-tert.-butyldimethylsilyl-3',3''-bis-O-desmethylavermectin B1a/B1b and 66 microliters of N,N-diisopropylethylamine in 140 microliters of dry methylene chloride. The reaction solution was stirred at room temperature, 23° C., for 12 hours and then diluted with methylene chloride. The methylene chloride solution was extracted with aqueous sodium bicarbonate, dried over sodium sulfate and evaporated under reduced pressure. The residue was chromatographed on silica gel plates using methylene chloride-methanol (99:1) furnishing 33 mg of 3'',5-di-O-tert.-butyldimethylsilyl-3',3''-bis-O-desmethyl-3',4''-di-O-methoxymethylavermectin B1a/B1b [FAB mass spectrum: (M+Li)+ =1123], which was further characterized by nuclear magnetic resonance, mass spectra and high pressure liquid chromatographic analyses.

EXAMPLE 20

3',3"-Bis-O-desmethyl-3',4"-di-O-methoxymethylavermectin B1a/B1b

A solution of 3",5-tert.-butyldimethylsilyl-3',3"-bis-O-desmethyl-3',4"-di-O-methoxymethylavermectin B1a/B1b, 33 mg, in 1.5 mL of anhydrous hydrogen fluoride-pyridine in tetrahydrofuran solution as described in EXAMPLE 5 was stirred at room temperature, 23° C., for 11 hours. Then aqueous sodium bicarbonate solution was added with stirring, and the product was extracted with methylene chloride. The methylene chloride solution was extracted with aqueous sodium bicarbonate, dried over sodium sulfate and evaporated under reduced pressure. The residue was chromatographed on silica gel plates using methylene chloride-methanol (97:3) furnishing 25.8 mg of 3',3"-bis-O-desmethyl-3',4"-di-O-methoxymethylavermectin B1a/B1b [939 (M+Li)+], which was fully characterized by nuclear magnetic resonance, mass spectra and high pressure liquid chromatographic analyses.

EXAMPLE 20a

If one uses the compounds 1a) through 5a) obtained as described fully in EP 276-131-A as starting materials for the procedure of EXAMPLE 18 and follows the procedures as described in EXAMPLEs 18, 19, and 20, the products 1b) through 5b) are obtained:

Starting materials:
1a) 3',3"-Bis-O-desmethyl-25-cyclohexyl-25-de-(2-butyl)avermectin B2a
2a) 3',3"-Bis-O-desmethyl-25-cyclopentyl-25-de-(2-butyl)avermectin B2a
3a) 3',3"-Bis-O-desmethyl-25-(3-thienyl)-25-de-(2-butyl)avermectin B2a
4a) 3',3"-Bis-O-desmethyl-25-(3-furyl)-25-de-(2-butyl)avermectin B2a
5a) 3',3"-Bis-O-desmethyl-25-(1-methylthioethyl)-25-de-(2-butyl)-avermectin B1a Reaction Products:
1b) 3',3"-Bis-O-desmethyl-25-cyclohexyl-25-de-(2-butyl)-3',4"-di-O-methoxymethylavermectin B2a
2b) 3',3"-Bis-O-desmethyl-25-cyclopentyl-25-de-(2-butyl)-3',4"-di-O-methoxymethylavermectin B2a
3b) 3',3"-Bis-O-desmethyl-25-(3-thienyl)-25-de-(2-butyl)-3',4"-di-O-methoxymethylavermectin B2a
4b) 3',3"-Bis-O-desmethyl-25-(3-furyl)-25-de-(2-butyl)-3',4"-di-O-methoxymethylavermectin B2a
5b) 3',3"-Bis-O-desmethyl-25-(1-methylthioethyl)-25-de-(2-butyl)-3',4"-di-O-methoxymethylavermectin B1a

EXAMPLE 21

5"-O-tert-Butyldimethylsilyl-3',3"-bis-O-desmethyl-3',4"-di-O-methoxymethylavermectin B1a/B1b A solution containing 240 mg of 3',3"-bis-O-desmethyl-3',4"-di-O-methoxymethylavermectin B1a/B1b, 47 mg of imidazole, and 52 mg of tert-butyldimethylsilyl chloride in 2.0 ml of dimethylformamide is stirred at room temperature for 45 minutes according to the procedure of EXAMPLE 1. Purification by preparative silica gel layer chromatography gives 5"-O-tert-butyldimethylsilyl-3',3"-bis-O-desmethyl-3',4"-di-O-methoxymethylavermectin B1a/B1b, which is characterized by its mass and NMR spectra.

EXAMPLE 22

5"-O-tert-Butyldimethylsilyl-3',3"-bis-O-desmethyl-3',4"-di-O-methoxymethyl-3"-oxoavermectin B1a/B1b 96 mg of 5"-O-tert-butyldimethylsilyl-3',3"-bis-desmethyl-3',4"-di-O-methoxymethylavermectin B1a is reacted according to the procedure of EXAMPLE 14 with 20 microliter of oxalyl chloride, 32 microliter of dimethylsulfoxide, and 0.15 ml of triethylamine in methylene chloride give the title compound, which is characterized by its mass and NMR spectra.

EXAMPLE 23

3"-Amino-3"-deoxy-5"-O-tert-Butyldimethylsilyl-3',3"-bis-O-desmethyl-3',4"-di-O-methoxymethylavermectin B1a/B1b A solution of 210 mg of 5"-O-tert-butyldimethylsilyl-3',3"-bis-O-desmethyl-3',4"-di-O-methoxymethyl-3"-oxoavermectin B1a/B1b and of 160 mg of ammonium acetate in 2.0 ml of methanol is reacted with 12 mg of sodium cyanoborohydride at room temperature for 100 minutes. Then 10 ml of an aqueous one half saturated sodium carbonate solution is added and the products are extracted with ethylacetate. The ethylacetate extract is washed with water, dried over magnesium sulfate, and concentrated in vacuo to a yellow glass. Purification by preparative silica gel layer chromatography gives 3"-amino-3"-deoxy-5"-O-tert-butyldimethylsilyl-3',3"-bis-O-desmethyl-3',4"-di-O-methoxymethylavermectin B1a/B1b, which is characterized by its mass and NMR spectra.

EXAMPLE 24

3"-Acetylamino-3"-deoxy-5"-O-tert-butyldimethylsilyl-3',3"-bis-O-desmethyl-3',4"-di-O-methoxymethylavermectin B1a/B1b A solution of 145 mg of 3"-amino-3"-deoxy-5"-O-tert-butyldimethylsilyl-3',3"-bis-O-desmethyl-3',4"-di-O-methoxymethylavermectin B1a in 1.25 ml of $CH_2Cl_2$ is treated with 16 microliter (17 mg, 1.2 equivalents) of acetic anhydride and kept at room temperature for 1 hour. Then the reaction mixture is diluted with ethyl acetate, washed with aqueous sodium bicarbonate and water, dried and concentrated in vacuo to a foam. Purification by preparative silica gel layer chromatography gives 3"-acetylamino-3"-deoxy-5"-O-tert-butyldimethylsilyl-3',3"-bis-O-desmethyl-3',4"-di-O-methoxymethylavermectin B1a/B1b, which is characterized by its mass and NMR spectra.

EXAMPLE 25

3"-Acetylamino-3"-deoxy-3',3"-bis-O-desmethyl-3',4"-di-O-methoxymethylavermectin B1a/B1b A solution 55 mg of 3"-acetylamino-3"-deoxy-5"-O-tert-butyldimethylsilyl-3',3"-bis-O-desmethyl-3',4"-di-O-methoxymethylavermectin B1a/B1b is deprotected with 50 mg of p-toluenesulfonic acid monohydrate in 5.0 ml of methanol according to the procedure of EXAMPLE 3 to give 3"-acetylamino-3"-deoxy-3',3"-bis-O-desmethyl-3',4"-di-O-methoxymethylavermectin B1a/B1b, which is characterized by its mass and NMR spectra.

EXAMPLE 26

4''-O-Acetyl-3',3'',5-tri-O-tert.-butyldimethylsilyl-3',3''-bis-O-desmethylavermectin B1a/B1b A solution of 3',3'',5-tri-O-tert.-butyldimethylsilyl-3',3''-bis-O-desmethylavermectin B1a/B1b, 55 mg, in 1.0 mL of pyridine and 0.5 mL of acetic anhydride was stirred at room temperature, 23° C., for 18 hours. The reaction solution was diluted with toluene and then concentrated under reduced pressure. The residue was taken up in methylene chloride, and the solution was washed with aqueous sodium bicarbonate, dried over sodium sulfate and concentrated under reduced pressure. The residue was chromatographed on silica gel plates furnishing 41 mg of 4''-O-acetyl-3',3'',5-tri-O-tert.-butyldimethylsilyl-3',3''-bis-O-desmethylavermectin B1a/B1b [1235(M+Li)+] which was characterized by nuclear magnetic resonance, mass spectra and high pressure liquid chromatographic analyses.

EXAMPLE 27

4''-O-Acetyl-3',3''-bis-O-desmethylavermectin B1a/B1b

4''-O-Acetyl-3',3'',5-tri-O-tert.-butyldimethylsilyl-3',3''-bis-O-desmethylavermectin B1a/B1b, 24 mg, was treated with 0.8 mL of anhydrous hydrogen fluoride-pyridine tetrahydrofuran as described in EXAMPLES 5 and 20. The residue from the methylene chloride solution was chromatographed on silica gel plates using methylene chloride-methanol (95:5) furnishing 7.5 mg of 4''-O-acetyl-3',3''-bis-O-desmethylavermectin B1a/B1b, [887(M+H)+], which was characterized by nuclear magnetic resonance, mass spectra and high pressure liquid chromatographic analyses.

EXAMPLE 28

3'-O-Desmethylavermectin B1a/B1b monosaccharide

A solution containing 2.11 g of 3',3''-bis-O-desmethylavermectin B1a/B1b in 20 ml of tetrahydrofuran is added slowly to a mixture of 4.6 ml of water, 4.6 ml of sulfuric acid and 17 ml of tetrahydrofuran stirred in an ice bath. The reaction mixture is left at room temperature for 18 hours, cooled again and poured onto ice and water. Extraction with methylenechloride, washing with aqueous sodium bicarbonate and water, drying and concentrated in vacuo gives a brown foam. Silica gel column chromatography with methylenechloride-ethylacetate solvent mixtures gives avermectin B1a/B1b aglycone and the desired 3'-O-desmethylavermectin B1a/B1b monosaccharide, which is characterized by its mass and NMR spectra.

EXAMPLE 29

3'-O-Desmethyl-3',5-di-O-tert-butyldimethylsilylavermectin B1a/B1b monosaccharide 3'-O-Desmethyl-3',5-di-O-tert-butyldimethylsilylavermectin B1a/B1b monosaccharide is obtained when 3'-O-desmethylavermectin B1a/B1b monosaccharide is reacted according to the procedure of EXAMPLE 18, and is characterized by its mass and NMR spectra.

EXAMPLE 30

3'-O-Desmethyl-3',5-di-O-tert-butyldimethylsilyl-4'-O-methoxymethylavermectin B1a/B1b monosaccharide 3'-O-Desmethyl-3',5-di-O-tert-butyldimethylsilyl-4'-O-methoxymethylavermectin B1a/B1b monosaccharide is obtained when 3'-O-desmethyl-3',5-di-O-tert-butyldimethylsilylavermectin B1a/B1b monosaccharide is reacted according to the procedure of EXAMPLE 19, and is characterized by its mass and NMR spectra.

EXAMPLE 31

3'-O-Desmethyl-4'-O-methoxymethylavermectin B1a/B1b monosaccharide

3'-O-Desmethyl-4'-O-Methoxymethylavermectin B1a/B1b monosaccharide is obtained when 3'-O-desmethyl-3',5-di-O-tert-butyldimethylsilyl-4'-O-methoxymethyl-avermectin B1a/B1b monosaccharide is reacted according to the procedure of EXAMPLE 20, and is characterized by its mass and NMR spectra.

What is claimed is:

1. A compound having the formula:

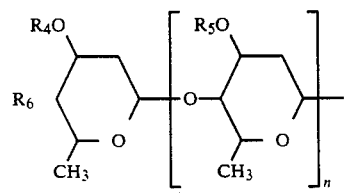
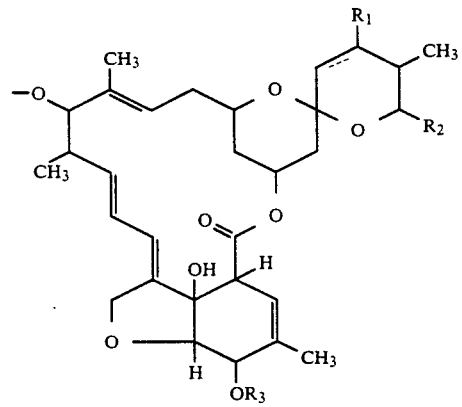

wherein the broken line at the 22,23 positions indicates that either a single or a double bond is present at the 22,23 position and that $R_1$ is present only when the broken line indicates a 22,23-single bond;

n is 0 or 1;

$R_1$ is hydrogen, hydroxy or a 23-oxo group;

$R_2$ is an α-branched $C_3$–$C_8$ alkyl, alkenyl, alkoxyalkyl or alkylthioalkyl; a $C_5$–$C_8$ cycloalkyl $C_1$–$C_4$ alkyl group, a $C_3$–$C_8$ cycloalkyl or a $C_5$–$C_8$ cycloalkenyl, each of which may be optionally substituted by methylene, or one or more $C_1$–$C_4$ alkyl groups or halogen; or a 3 to 6 membered oxygen or sulfur containing heterocycle which may be saturated or fully or partly unsaturated and which may be substituted by one or more $C_1$–$C_4$ alkyl groups or halogen atoms;

$R_3$ is hydrogen, methyl, loweralkanoyl, loweralkoxycarbonyl, or triloweralkylsilyl;

$R_4$ and $R_5$ are independently hydrogen, methyl, loweralkanoyl, benzoyl, loweralkoxycarbonyl, phenoxycarbonyl, carbamoyl, N-loweralkylcarbamoyl, N,N-diloweralkyl-carbamoyl or loweralkoxy loweralkyl, provided that both $R_4$ and $R_5$ are not simultaneously methyl; and $R_6$, with the broken line indicating a single bond to $R_6$ is N-loweralkanoyl-N-loweralkylamino, loweralkoxycarbonylamino, triloweralkylsilyloxy, loweralkoxymethoxy, succinoyloxy or acetylglycyloxy; or, when the broken line indicates a double bond to $R_6$, $R_6$ is, semicarbazono, loweralkanoyl hydrazono, benzoyl hydrazono, loweralkyl substituted benzoyl hydrazono or p-toluene sulfonylhydrazono.

2. The compounds of claim 1 wherein:

$R_1$ is hydrogen or hydroxy;

$R_2$ is an alpha-branched $C_3$–$C_8$ alkyl or alkenyl group; and $R_3$ is hydrogen or methyl;

$R_4$ and $R_5$ are independently hydrogen, methyl, loweralkanoyl, benzoyl, loweralkoxycarbonyl or loweralkoxyloweralkyl provided that both $R_4$ and $R_5$ are not simultaneously methyl; and $R_6$, with the broken line indicating a single bond is, N-loweralkanoyl-N-loweralkylamino or loweralkoxymethoxy.

3. The compounds of claim 1 wherein $R_1$ is hydrogen or hydroxy;

$R_2$ is 2-propyl, 2-butyl, 2-pentyl, 2-hexyl, 2-buten-2-yl, 2-penten-2-yl, 4-methyl-2-penten-2-yl, cyclohexyl, cylcopentyl, 3-thienyl, 3-furyl or 1-methylthioethyl;

$R_3$ is hydrogen;

$R_4$ and $R_5$ are independently hydrogen, methyl, loweralkanoyl, loweralkoxyloweralkyl, loweralkoxycarbonyl, carbamoyl, N-loweralkylcarbamoyl or N,N-diloweralkylcarbamoyl, provided that both $R_4$ and $R_5$ are not simultaneously methyl; and;

$R_6$, with broken line indicating a single bond, is ethoxymethoxy; succinoyloxy, or acetylglycyloxy.

4. The compounds of claim 1 wherein both $R_4$ and $R_5$ are other than hydrogen or methyl.

5. The compound of claim 3 which is 3′,3″-bis-O-desmethyl-3′,4″-di-O-methoxymethyl avermectin B1a/B1b.

6. The compound of claim 3 which is 3″-O-desmethyl-22,23-dihydro-4″-O-methoxymethyl avermectin B1a/B1b.

7. The compound of claim 3 which is 3″-acetylamino-3′,3″-bis-O-desmethyl-3′,4″-di-O-methoxymethyl avermectin B1a/B1b.

8. A method for the treatment of helmintic or parasitic infections in animals infected with helminths or parasites which comprises administering to such animals an effective amount of a compound of claim 1.

9. A method for the treatment of parasites of plants infected with parasites which comprises applying to such plants, to the soil in which they grow, or to the crops harvested therefrom, and effective amount of a compound of claim 1.

10. A composition useful for the treatment of parasitic diseases of plants or animals which comprises an inert carrier and an effective amount of a compound of claim 1.

* * * * *